United States Patent [19]

Cheung

[11] Patent Number: 5,096,681
[45] Date of Patent: Mar. 17, 1992

[54] REMOVAL OF TRIALKYL ARSINE FROM FLUIDS

[75] Inventor: Tin-Tack P. Cheung, Bartlesville, Okla.

[73] Assignee: Phillips Petroleum Company, Bartlesville, Okla.

[21] Appl. No.: 659,799

[22] Filed: Feb. 22, 1991

[51] Int. Cl.$^5$ .................... B01D 53/14; C07C 7/12
[52] U.S. Cl. .................... 423/245.1; 423/210; 585/823
[58] Field of Search ............ 423/245.1, 245.3, 210, 423/245.2, 592; 585/823

[56] References Cited

U.S. PATENT DOCUMENTS

| | | | |
|---|---|---|---|
| 3,812,652 | 5/1974 | Carr et al. | 55/68 |
| 4,048,387 | 9/1977 | Lahme et al. | 429/50 |
| 4,462,896 | 7/1984 | Kitagawa et al. | 585/823 |
| 4,532,115 | 7/1985 | Nishino et al. | 423/210 |
| 4,578,256 | 3/1986 | Nishino et al. | 423/210 |
| 4,593,148 | 6/1986 | Johnson et al. | 585/823 |
| 4,605,812 | 8/1986 | Nowack et al. | 585/845 |
| 4,752,379 | 5/1988 | Delaney | 208/251 R |
| 4,839,029 | 6/1989 | Ichikawa et al. | 208/251 R |
| 4,861,939 | 8/1989 | Debras et al. | 423/210 |
| 4,933,159 | 6/1990 | Nowack et al. | 423/245.1 |
| 4,962,272 | 10/1990 | Cullo et al. | 585/820 |
| 4,971,608 | 11/1990 | Tooley et al. | 55/72 |
| 4,992,620 | 2/1991 | Nowack et al. | 585/820 |
| 5,024,683 | 6/1991 | Tolley et al. | 55/74 |

FOREIGN PATENT DOCUMENTS

| | | | |
|---|---|---|---|
| 57-77627 | 5/1982 | Japan | 423/210 |
| 60-68034 | 9/1983 | Japan | |
| 62-95119 | 5/1987 | Japan | 423/210 |
| 62-286524 | 12/1987 | Japan | 423/210 |

OTHER PUBLICATIONS

Irgolic, K. J. "Determination of Arsenic and Arsenic Compounds in Natural Gas Samples," *Applied Organic-Metallic Chemistry*, vol. 5 (1991), pp. 117–124.

Patent Abstracts of Japan, Group #C576, vol. 13, #107, Published Mar. 14, 1989 (JP-63-283725).

*Primary Examiner*—Gregory A. Heller
*Assistant Examiner*—Peter DiMauro
*Attorney, Agent, or Firm*—K. K. Brandes

[57] ABSTRACT

Trialkyl arsine (in particular trimethyl arsine) is removed from a fluid (e.g., a hydrocarbon-containing gas) by contacting the fluid with a sorbent material comprising vanadium pentoxide ($V_2O_5$) and an inorganic support material (preferably alumina or silica or vanadium metal).

16 Claims, No Drawings

5,096,681

REMOVAL OF TRIALKYL ARSINE FROM FLUIDS

BACKGROUND OF THE INVENTION

This invention relates to the removal of trialkyl arsines from fluids by means of solid sorbents. In another aspect, this invention relates to the removal of trialkyl arsines from gases, in particular hydrocarbon-containing gases.

Materials for adsorbing and/or absorbing unsubstituted arsine ($AsH_3$) are well known. However, many of these materials are ineffective for the sorption of trialkyl arsines, which may be present as undesirable impurities in natural gas streams produced at some well sites. The present invention provides a sorbent material which is effective for removing trialkyl arsines from fluids by sorption (i.e., adsorption and/or absorption).

SUMMARY OF THE INVENTION

It is an object of this invention to provide a process for removing trialkyl arsines from fluids. It is another object of this invention to provide a process for removing trialkyl arsines from gases, in particular hydrocarbon-containing gases. Other objects will become apparent from the detailed description of the invention and the appended claims.

In accordance with this invention, a process for at least partially removing trialkyl arsines from fluids (preferably gases) comprises the step of contacting a fluid feed which contains at least one trialkyl arsine with a solid sorbent material comprising (preferably consisting essentially of) vanadium pentoxide, deposited on an inorganic support material (preferably selected from the group consisting of alumina, fluorided alumina, aluminum phosphate, magnesia, silica, aluminosilicates, titania, zirconia, hafnia, zinc oxide, zinc aluminate, aluminates of metals of Group IIA of the Periodic Table [as defined on page 852 of Webster's New Collegiate Dictionary, 1977], zinc titanate, titanates of Group IIA metals, vanadium metal and activated carbon, and mixtures of the above materials); wherein said contacting is carried out at such contacting conditions as to obtain a fluid product having a lower trialkyl arsine content than said feed (with the spent sorbent material containing the portion of trialkyl arsine which has been removed from the feed). Preferred sorbent materials are vanadium pentoxide on alumina as support, vanadium pentoxide on silica as support, and vanadium pentoxide on vanadium metal as support.

DETAILED DESCRIPTION OF THE INVENTION

The term "trialkyl arsine", as used herein, refers to compounds having the general chemical formula of $R_3As$, wherein each R is a radical independently selected from among alkyl groups (straight and/or branched), preferably having 1-6 (more preferably 1-3) carbon atoms. Particularly preferred trialkyl arsines are trimethyl arsine, triethyl arsine, dimethyl ethyl arsine and diethyl methyl arsine.

Any suitable liquid or gaseous fluid stream which contains trialkyl arsine(s) can be used as feed in the process of this invention. Preferably, the feed is gaseous. Non-limiting examples of suitable feeds are: natural gas; gaseous petroleum fractions comprising paraffins and olefins containing 1-6 carbon atoms per molecule; and gaseous products from thermal and catalytic cracking of petroleum, shale oil or coal. Generally, the gases comprise methane, ethane, ethylene, propane, propylene, n-butane, isobutane, butenes; and the like. These gas streams can contain other impurities, such as hydrogen sulfide, carbonyl sulfide (COS), mercaptans, organic sulfides, mercury and/or compounds thereof, carbon monoxide, carbon dioxide, inert gases ($N_2$, He, Ne, Ar), and the like.

Other arsenic compounds may also be present in the fluid stream which is treated by the process of this invention, such as $AsH_3$, $RAsH_2$, $R_2AsH$, and the like, wherein R is an alkyl group, as defined above. It is also possible to have triphenyl arsine, dialkyl phenyl arsines, dialkyl cycloalkyl arsines, and the like present in the feed.

Generally, the total concentration of the trialkyl arsine(s) in the feed (preferably gaseous) is in the range of from about 1 ppb As (1 part by weight arsenic per billion parts by weight of feed) to about 0.1 weight-% As, preferably about 0.01-10 ppm As (0.01-10 parts by weight arsenic per million parts by weight of feed). The concentrations of the other impurities and the exact composition of the feed will widely vary from feedstock to feedstock.

The sorbent material employed in the process of this invention is supported vanadium pentoxide ($V_2O_5$). When a supported vanadium oxide is used, the weight percentage of V (present as pentoxide) in the sorbent material generally is in the range of from about 1 to about 20 weight-% V, preferably about 2-15 weight-% V.

Any suitable, effective inorganic support material can be combined with $V_2O_5$. Preferably, the support material is selected from the group consisting of alumina, fluorided alumina (i.e., alumina which has been treated with HF or $NH_4HF_2$ under such conditions as to incorporate fluoride ions into the crystal lattice of alumina), aluminum phosphate, magnesia (MgO), silica, aluminosilicates (such as clays and zeolites), titania ($TiO_2$), zirconia ($ZrO_2$), hafnia ($HfO_2$), zinc oxide, zinc aluminate ($ZnAl_2O_4$) aluminates of Group IIA metals (i.e., of Be, Mg, Ca, Sr, Ba), zinc titanate ($Zn_2TiO_4$), titanates of Group IIA metals, vanadium metal, activated carbon, and mixtures of two or more than two of the above materials. The presently more preferred support material is alumina.

Vanadium pentoxide and the inorganic support material can be combined in any suitable manner. In a presently more preferred method, the inorganic support material is impregnated with a solution (preferably aqueous) of a vanadium compound. The thus impregnated material is dried and then calcined (generally in air, preferably for about 1-20 hours at about 470°-750° C.) so as to substantially decompose the vanadium compound to $V_2O_5$.

The solid sorbent particles of this invention can have any suitable surface area (preferably about 10-1000 $m^2/g$, as measured by the B.E.T. method employing $N_2$), any suitable shape (such as spherical, cylindrical, ring-shaped, trilobal etc.), and any suitable size (such as about 0.2-20 mm diameter for spherical particles).

Any suitable contacting conditions can be employed in the sorption process of this invention. Generally, the temperature in the contacting zone is in the range of from about −20° to about 100° C., preferably about 20° to about 50° C. Generally, the pressure in the contacting zone is in the range of from about 1 to about 500 atm., preferably about 1 to about 70 atm. Generally, the gas hourly space velocity of the gaseous feed in the contacting zone is in the range of from about 10 to about 20,000 volume of feed/volume of sorbent/hour, preferably about 1,000 to about 10,000 volume/volume/hour, measured at about 25° C./1 atm. Generally, the contacting is continued until trialkyl arsine breakthrough occurs, i.e., when the treated product contains more trialkyl arsines than can be tolerated, such as about 50 ppb.

Treatment of the feed streams in accordance with the process of this invention can be carried out in any suitable manner. For example, in a preferred embodiment a bed of the sorbent is placed as a fixed bed in a confined zone, and a fluid stream (preferably a gas) is passed therethrough in either upward or downward flow. Other suitable, yet less preferred methods of treatment can include a fluidized operation in which the feed and the sorbent particles are maintained in a state of turbulence under hindered settling conditions in a confined zone, moving bed operations in which the sorbent passes as a moving bed countercurrently to or concurrently with the feed, etc. In a fixed bed operation of a continuous process, the flow of fluid can be rotated between two or more sorbent beds with at least one being in regular operation, the other being in a regeneration mode. Continuous processes are preferred, but it is understood that batch type operations can be employed when desired.

It is within the scope of this invention to employ a combination of sorbents, such as a first bed (guard bed) of a supported CuO-ZnO material (described in U.S. Pat. No. 4,593,148) or $PbO/Al_2O_3$ for substantial removal of $AsH_3$ and/or $H_2S$ from the feed, and at least one subsequent downstream bed containing the sorbent material of this invention for absorbing trialkyl arsines. This multi-bed operation can be carried out in one reactor containing a layer of the supported CuO-ZnO material or $PbO/Al_2O_3$ (or any other known sorbent for $AsH_3$ and $H_2S$) and a downstream layer of a trialkyl arsine sorbent of this invention. Or the multi-bed operation can be carried out using two (or more) separate sorption reactors: a first reactor containing the supported CuO-ZnO material or $PbO/Al_2O_3$ (or any other known sorbent for $AsH_3$ and $H_2S$) and a second reactor containing the trialkyl arsine sorbent of this invention, wherein the feed passes through the first reactor and thereafter through the second reactor.

The process of this invention will be further illustrated by the following non-limiting examples.

EXAMPLE I

This example illustrates the preparation of two preferred sorbent materials and the experimental setup for investigating the sorption of trimethyl arsine (TMA) by these sorbent materials.

Sorbent A was vanadium pentoxide on silica having been prepared as follows. 50 grams of silica gel (marketed by Davison Chemical Division, W. R. Grace and Co., Baltimore, Md., under the product designation of "Davisil") were soaked with an aqueous solution containing 9.8 g $VOSO_4 \cdot 2H_2O$ in 100 cc water. The thus-impregnated silica was dried by heating on a hot plate and then calcined in air for about 16 hours at a temperature of about 665° C. Calcined Sorbent A contained 3.1 weight-% V and had a surface area of 275 $m^2/g$.

Sorbent B was vanadium pentoxide on alumina having been prepared as follows. Ten grams of a 30–60 mesh alumina (marketed by Aluminum Company of America, Pittsburgh, Pa., under the product designation of "S-201") were impregnated with 10 cc of a hot aqueous solution containing 1.5 grams of sodium metavanadate, followed by drying. The dried material was impregnated again with 10 cc of the above sodium metavanadate solution, followed by drying and calcining in air at 500° C. for about 16 hours. Calcined Sorbent B contained 9.6 weight-% V.

A nitrogen gas stream was passed through a flask containing liquid trimethyl arsine (provided by Strem Chemicals, Inc., Newburyport, Mass.), which was cooled to about $-78°$ C. by placing the flask in a dry ice/acetone mixture. The exiting gas stream, which contained $N_2$ and about 0.066 weight-% trimethyl arsine, was passed through a glass tube of about 7 mm diameter and about 12 cm length containing about 1 gram of Sorbent A or B. The gas which exited from the absorption tube was passed through an aqueous solution of $KMnO_4$ and then to a flow meter. The flow rate of the gas was about 1800 cc/hour (equivalent to about 360 cc/cc sorbent/hour).

When trimethyl arsine breakthrough occurred (i.e., when the sorbent had reached its maximum arsine absorption capacity), the purple color of the $KMnO_4$ solution turned brownish. After arsine breakthrough had been detected, the flow of the trimethyl arsine containing gas stream was stopped, and a purge stream of pure nitrogen was passed through the sorbent material for about 15 hours so as to purge unabsorbed trimethyl arsine therefrom. The sorption tube containing the sorbent and adsorbed/absorbed trimethyl arsine was weighed. The difference between this weight and the initial weight of the tube with fresh sorbent was the weight of adsorbed and/or absorbed trimethyl arsine.

Sorbent A contained about 0.020 gram of trimethyl arsine per gram sorbent when trimethyl arsine breakthrough had occurred, while Sorbent B had adsorbed 0.0185 gram trimethyl arsine per gram sorbent. The atomic ratio of As to V in the spent sorbents was about 1–2:10.

EXAMPLE II

This example illustrates the adsorption of trimethyl arsine by $V_2O_5$ prepared by oxidation of a vanadium metal foil.

A vanadium foil was exposed to ultrapure oxygen (400 torr) at 200° C. for about 1 hour in a stainless steel bell jar, which was attached (but not connected), to an X-ray photoelectron spectrometer (a PHI-500 ESCA/Auger spectrometer equipped with an aluminum X-ray source). Thereafter, the bell jar was evacuated to about $10^{-9}$ torr and connected to the spectrometer. The spectrum of the oxidized vanadium foil was measured. From the positions of the XPS emission peaks it was concluded that the surface coating of the metal foil consisted essentially of $V_2O_5$.

Then the bell jar was filled with nitrogen gas which contained 0.066% trimethyl arsine (TMA). After exposure of the oxidized vanadium foil to the $N_2$/TMA gas mixture for about 15 minutes at 25° C./800 torr, the bell jar was evacuated again and reconnected to the spectrometer. The spectrometer was operated at a pass energy of 25 eV. Evaluation of XPS peaks and their intensities revealed that trimethyl arsine had been adsorbed by $V_2O_5$ on vanadium metal, and that the molar ratio of adsorbed trimethyl arsine to $V_2O_5$ on the sorbent surface was about 0.06:1.

Reasonable variations and modifications which will be apparent to those skilled in the art, can be made within the scope of the disclosure and appended claims without departing from the scope of this invention.

That which is claimed is:

1. A process for at least partially removing trialkyl arsines from gases comprising the step of contacting a gaseous feed which contains at least one trialkyl arsine with a solid sorbent material consisting essentially of vanadium pentoxide and vanadium metal as support material, wherein said contactin is carried out at such contacting conditions as to obtain a product having a lower trialkyl arsine content than said feed, and wherein the content of said at least one trialkyl arsine in said feed is such as to provide a level of about 1 ppb to about 0.1 weight-% As.

2. A process in accordance with claim 1, wherein said feed is a hydrocarbon-containing gas.

3. A process in accordance with claim 1, wherein said trialkyl arsine has the chemical formula of $R_3As$ with each R being independently selected from the group consisting of alkyl groups containing 1-6 carbon atoms.

4. A process in accordance with claim 3, wherein said alkyl groups contain 1-3 carbon atoms.

5. A process in accordance with claim 1, wherein said at least one trialkyl arsine is selected from the group consisting of trimethyl arsine, triethyl arsine, dimethyl ethyl arsine and diethyl methyl arsine.

6. A process in accordance with claim 1, wherein said contacting is carried out at a temperature in the range of about $-20°$ C. to about $100°$ C.

7. A process for at least partially removing trialkyl arsines from gases comprising the step of contacting a gaseous feed which contains at least one trialkyl arsine with a solid sorbent material consisting essentially of vanadium pentoxide and at least one support material selected from the group consisting of silica, alumina, fluorided alumina, aluminum phosphate, magnesia, aluminosilicates, titania, zirconia, hafnia, zinc oxide, zinc aluminate, aluminates of Group IIA metals, zinc titanate, titanates of Group IIA metals, activated carbon, and mixtures thereof, wherein said contacting is carried out at such contacting conditions as to obtain a product having a lower trialkyl arsine content than said feed, and wherein the content of said at least one trialkyl arsine in said feed is such as to provide a level of about 1 ppb to about 0.1 weight-% As.

8. A process in accordance with claim 7, wherein said feed is a hydrocarbon-containing gas.

9. A process in accordance with claim 7, wherein said trialkyl arsine has the chemical formula of $R_3As$ with each R being independently selected from the group consisting of alkyl groups containing 1-6 carbon atoms.

10. A process in accordance with claim 9, wherein said alkyl groups contain 1-3 carbon atoms.

11. A process in accordance with claim 7, wherein said at least one trialkyl arsine is selected from the group consisting of trimethyl arsine, triethyl arsine, dimethyl ethyl arsine and diethyl methyl arsine.

12. A process in accordance with claim 7, wherein said contacting is carried out at a temperature in the range of about $-20°$ C. to about $100°$ C.

13. A process in accordance with claim 7, wherein said sorbent material has been prepared by a method which comprises impregnating said at least one support material with a solution of a vanadium compound, drying the obtained vanadium-impregnated material, and calcining the dried, vanadium-impregnated material at about $470°-750°$ F. so as to substantially decompose said vanadium compound to vanadium pentoxide.

14. A process in accordance with claim 7, wherein the content of vanadium pentoxide in said sorbent material is such as to provide a level of about 1 to about 20 weight-% V.

15. A process in accordance with claim 7, wherein said at least one support material is alumina.

16. A process in accordance with claim 7, wherein said at least one support material is silica.

* * * * *